US009282906B2

(12) United States Patent
Sugo et al.

(10) Patent No.: US 9,282,906 B2
(45) Date of Patent: Mar. 15, 2016

(54) BLOOD VOLUME MEASURING METHOD AND BLOOD VOLUME MEASURING APPARATUS

(75) Inventors: Yoshihiro Sugo, Tokyo (JP); Mitsushi Hyogo, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1550 days.

(21) Appl. No.: 12/878,336

(22) Filed: Sep. 9, 2010

(65) Prior Publication Data
US 2011/0060531 A1 Mar. 10, 2011

(30) Foreign Application Priority Data
Sep. 8, 2009 (JP) ................................. 2009-207446

(51) Int. Cl.
| A61B 5/026 | (2006.01) |
|---|---|
| A61B 5/029 | (2006.01) |
| A61B 5/0225 | (2006.01) |
| A61B 5/0285 | (2006.01) |

(52) U.S. Cl.
CPC ............... *A61B 5/029* (2013.01); *A61B 5/0285* (2013.01); *A61B 5/02255* (2013.01)

(58) Field of Classification Search
CPC .................................................... G01F 13/006
USPC .......................................................... 482/13
See application file for complete search history.

(56) References Cited

U.S. PATENT DOCUMENTS

| 5,908,392 | A * | 6/1999 | Wilson | A61N 1/3702 600/509 |
|---|---|---|---|---|
| 6,408,198 | B1 * | 6/2002 | Hanna | A61B 5/7214 600/323 |
| 7,402,138 | B2 * | 7/2008 | Sugo et al. | 600/526 |
| 7,725,183 | B1 * | 5/2010 | Knight | A61N 1/025 607/9 |
| 2003/0167010 | A1 * | 9/2003 | Pinsky | A61B 5/02007 600/485 |
| 2004/0087863 | A1 | 5/2004 | Eide | |
| 2005/0090753 | A1 * | 4/2005 | Goor | A61B 5/02028 600/508 |
| 2005/0187481 | A1 * | 8/2005 | Hatib | A61B 5/02 600/485 |
| 2005/0222514 | A1 | 10/2005 | Sugo | |
| 2007/0179386 | A1 | 8/2007 | Michard et al. | |
| 2008/0300494 | A1 * | 12/2008 | Hatib et al. | 600/485 |
| 2010/0324428 | A1 | 12/2010 | Pfeiffer | |
| 2011/0270047 | A1 * | 11/2011 | O'Brien | 600/301 |

FOREIGN PATENT DOCUMENTS

| EP | 0 947 160 A1 | 10/1999 |
|---|---|---|
| EP | 1 434 141 A2 | 6/2004 |
| JP | 2004-105682 A | 4/2004 |
| JP | 2004-188038 A | 7/2004 |

(Continued)

OTHER PUBLICATIONS

Extended European Search Report dated Nov. 25, 2010 for EP 10 17 5153.

(Continued)

*Primary Examiner* — Toan Le
*Assistant Examiner* — Jeffrey Aiello
(74) *Attorney, Agent, or Firm* — Kenealy Vaidya LLP

(57) ABSTRACT

A blood volume measuring method, apparatus and program for removing an artifact when used in an apparatus for analyzing respiratory variation of the stroke volume of a patient in order to determine the fluid response of the patient or adequately set artificial ventilation is provided.

9 Claims, 11 Drawing Sheets

(56) References Cited

FOREIGN PATENT DOCUMENTS

| | | | |
|---|---|---|---|
| JP | 2005-124718 A | | 5/2005 |
| JP | 2005124718 A | * | 5/2005 |
| JP | 2005-312947 A | | 11/2005 |
| JP | 2007-203041 A | | 8/2007 |
| WO | 91/00053 A1 | | 1/1991 |
| WO | 97/24982 A1 | | 7/1997 |
| WO | 2009/100927 A1 | | 8/2009 |

OTHER PUBLICATIONS

Japanese Office Action for the related Japanese Patent Application No. 2009-207446 dated Aug. 2, 2013.

European Office Action for the related European Patent Application No. 10 175 153.5 dated Jul. 2, 2015.

* cited by examiner

BLOOD VOLUME MEASURING METHOD AND BLOOD VOLUME MEASURING APPARATUS

BACKGROUND OF THE INVENTION

The present invention relates to a blood volume measuring method and a blood volume measuring apparatus, particular to method, apparatus and program of removing an artifact in an apparatus for analyzing respiratory variation of the stroke volume of the patient in order to determine the fluid response of the patient or adequately set artificial ventilation.

There are related-art methods of analyzing respiratory variation of the stroke volume of the patient. In a first method, the stroke volume is measured from variation of the pulse wave propagation time by using correlation between the pulse wave propagation time and the stroke volume (see JP-A-2005-312947), and respiratory variation is analyzed from the acquired stroke volume.

JP-A-2005-312947 discloses the following biological signal monitoring apparatus shown in FIG. 8. FIG. 8 is a block diagram illustrating the configuration of the related-art biological signal monitoring apparatus, and FIG. 9 is a diagram illustrating an example of the manner of measurement in the related-art biological signal monitoring apparatus. FIG. 10 is a view showing waveforms of pulse waves which are measured by the related-art biological signal monitoring apparatus.

As shown in FIG. 9, a systole/diastole blood pressure measuring unit 120 is configured by a cuff 125, a compressing pump 127, a pressure sensor 128, a cuff pressure detector 129, an A/D converter 122, etc.

Specifically, as shown in FIG. 9, the cuff 125 is attached to an upper arm of the patient for measurement. In the cuff 125, the interior is opened or closed with respect to the atmosphere by an exhaust valve 126 installed in the body 110 of the biological signal monitoring apparatus. Air is supplied to the cuff 125 by the compressing pump 127 installed in the body 110. The pressure sensor 128 is mounted in the body 110, and an output of the pressure sensor 128 is detected by the cuff pressure detector 129. An output of the cuff pressure detector 129 is converted into a digital signal by the A/D converter 122, and input to a cardiac output calculating unit 140. In FIG. 9, the cuff pressure detector 129, the A/D converter 122, and the cardiac output calculating unit 140 are included in the body 110.

In FIG. 10, (a) shows an electrocardiogram waveform, and an aortic pressure wave immediately after the ejection from the heart has a waveform shown by (b). Further, waveforms of an arterial pressure wave at the periphery and a peripheral pulse wave are acquired as shown by (c) and (d).

As shown in FIG. 8, a pulse wave propagation time measuring unit 130 is configured by a time interval detection reference point measuring unit 131, an A/D converter 132, a photoplethysmogram sensor 133, a pulse wave detector 134, an A/D converter 135, etc.

The time interval detection reference point measuring unit 131 is used for detecting a point of time when an R wave is generated on an electrocardiogram, and an output thereof is converted into a digital signal by the A/D converter 132, and then input to the cardiac output calculating unit 140. Specifically, the time interval detection reference point measuring unit 131 is configured by ECG electrodes 131a which are attached to the chest of the patient, as illustrated in FIG. 9. Measurement data is transmitted from a measurement data transmitter 150 which is electrically connected to the ECG electrodes 131a, to the body 110 in a wireless manner. The transmitted measurement data is converted into a digital signal by the A/D converter 132 in the body 110, and then input to the cardiac output calculating unit 140. In this way, the ECG waveform as shown by (a) of FIG. 10 is acquired.

Meanwhile, the photoplethysmogram sensor 133 is intended to be attached to a peripheral part, such as a finger, of the patient, as shown in FIG. 9, and to be used in acquiring the pulse wave propagation time, for example, by performing SpO2 measurement. The photoplethysmogram sensor 133 is electrically connected to the measurement data transmitter 150, and the measurement data transmitter 150 transmits the measurement data to the body 110 in a wireless manner. When the measurement data is sent to the pulse wave detector 134 in the body 110 of the biological signal monitoring apparatus, the pulse wave (photoplethysmogram) at the attachment location of the patient is detected. The output of the pulse wave detector 134 is converted into a digital signal by the A/D converter 135 and then input to the cardiac output calculating unit 140. As such, a waveform of the photoplethysmogram (a waveform at the periphery) such as shown by (d) of FIG. 10 is acquired.

Next, a calculation process of acquiring esCO from an expression of $esCO = (\alpha K \cdot PWTT + \beta K) \cdot HR$ will be described with reference to the flowchart of FIG. 11. In the expression, esCO is an estimated cardiac output, PWTT is a pulse wave propagation time, HR is the heart rate, and $\alpha$, $\beta$, and K are coefficients inherent to the patient. FIG. 11 shows the procedure in which $\beta K$ is acquired by calibration using an initial value of $\alpha K$ and then the estimated cardiac output esCO is calculated.

Reading of the initial value of $\alpha K$ is carried out (Step S31).

PWTT and HR are acquired (Step S32).

Next, it is determined whether $\beta K$ is available or not (Step S33).

If the determination in Step S33 is NO, then a request for input of CO value for calibration is displayed (Step S34).

It is determined whether the CO value for calibration has been input or not (Step S35).

If the determination in Step S35 is YES, the input CO value, and the acquired PWTT and HR are stored in a register as CO1, PWTT1, and HR1, respectively (Step S36).

$\beta K$ is acquired from an expression of $\beta K = CO1/HR1 - \alpha K \cdot PWTT1$ (step S37).

Calculation of acquiring esCO from the expression of $esCO = (\alpha K \cdot PWTT + \beta K) \cdot HR$ is carried out by using the acquired $\beta K$ (step S38).

If the determination in Step S33 is YES, likewise, calculation of acquiring esCO from $esCO = (\alpha K \cdot PWTT + \beta K) \cdot HR$ is carried out (Step S38).

The esCO acquired in the calculation is displayed (step S39).

The above process is repeated as required.

From the above esCO, the estimated stroke volume esSV is acquired by using an expression of $esSV = esCO/HR$.

From the above eeSV, variation of stroke volume (SVV) is acquired by using an expression of $SVV = 2 \cdot (esSVmax - esSVmin)/(esSVmax + esSVmin)$. In the expression, esSVmax is the maximum estimated stroke volume per respiratory rate and esSVmin is the minimum estimated stroke volume per respiratory rate.

In a second method, the pulse pressure of the blood pressure of the patient is measured by using correlation between the stroke volume and the blood pressure, to measure respiratory variation of the stroke volume (see JP-A-2007-203041). In JP-A-2007-203041, arterial pulsation pressure variation (PPV) is acquired from an expression of $PPV = 2 \cdot (PPmax - PPmin)/(PPmax + PPmin)$. In the expression, PPmax is the maximum arterial pulsation pressure (PP) per respiratory rate, and PPmin is the minimum arterial pulsation pressure (PP) per respiratory rate.

PPV is calculated with respect to respiratory rates without arrhythmia. When the variability of at least three continuous PPV values (defined as the standard deviation divided by the average value of the arterial pulsation pressure variation PPV) is larger than a predetermined threshold (for example, 15%), the corresponding PPV values are determined to be inadequate, and omitted from dynamic analysis of the blood pressure.

A third method is the PAD (Pulse Amplitude Deviation) method in which, by using correlation between the amplitude of a peripheral pulse wave and the stroke volume, respiratory variation of the stroke volume is measured from variation of the pulse wave amplitude (see JP-A-2004-105682). In JP-A-2004-105682, the pulse wave amplitude variation (PAV) is acquired by an expression of PAV=100·(Pmax−Pmin)/meanP. In the expression, Pmax is maximum pulse wave amplitude per respiratory rate, Pmin is minimum pulse wave amplitude per respiratory rate, and meanP is average pulse wave amplitude per respiratory rate.

In the first method where respiratory variation of the stroke volume is measured from variation of the pulse wave propagation time by using correlation between the pulse wave propagation time and the stroke volume, there is a difference between the measurement resolutions of an ECG and a pulse oximetry plethysmogram and the measurement resolution of the pulse wave propagation time. In the case where the measurement resolution of an ECG is 4 msec and that of a pulse oximetry plethysmogram is 8 msec, for example, the measurement resolution of the pulse wave propagation time is 3 to −7 msec, and insufficient. Therefore, the process requires an A/D converter which has a higher measurement resolution of, for example, about 1 msec. Since an ECG and a pulse oximetry plethysmogram are used, there is a problem in that the method is sensitive to an artifact.

In the second method, the minimum resolution of the blood pressure which is usually used in clinic is about 1 mmHg, and requested resolution is not so high. In the second method where, by using correlation between the stroke volume and the blood pressure, the pulse pressure of the blood pressure of the patient is measured to measure respiratory variation of the stroke volume, by contrast, the blood pressure is directly measured by using an arterial catheter, and hence there is a problem in that the measurement of the blood pressure waveform may be often interrupted by zero balance, flash, or the like, and the interrupted portion must be omitted from the analysis.

In the third method which is the PAD (Pulse Amplitude Deviation) method where, by using correlation between the amplitude of a peripheral pulse wave and the stroke volume, respiratory variation of the stroke volume is measured from variation of the pulse wave amplitude, the pulse wave amplitude is largely varied depending on the peripheral circulation and vasomotor innervation, and changed in the range of 100 or more times. In order to cope with a high-amplitude pulse wave while ensuring the resolution required for a low-amplitude pulse wave, therefore, an A/D converter having a wide dynamic range and a high resolution is necessary. In a pulse oximetry plethysmogram, the signal level is low, and the measurement is performed on the surface of the body. Therefore, there is a problem in that the method is sensitive to an artifact.

SUMMARY

It is therefore an object of the invention to provide a method, apparatus and program of removing an artifact which, in an apparatus for analyzing respiratory variation of the stroke volume of the patient in order to determine the fluid response of the patient or adequately set artificial ventilation, can accurately remove an artifact without requiring an expensive A/D converter having a high resolution.

In order to achieve the object, according to the invention, there is provided a blood volume measuring method comprising: acquiring data of stroke volume variation at each respiratory rate, and storing the acquired data in a first buffer; reading an N1 number of the data stored in the first buffer, from the first buffer, and storing the N1 number of the data in a second buffer; excluding a part of the data stored in the second buffer, a value of each of which exceeds a first upper limit or falls below a first lower limit, from the data stored in the second buffer, and storing the other of the data stored in the second buffer, in a third buffer; acquiring a deviation of each of the data stored in the third buffer, from a median value of the data stored in the third buffer, excluding a part of the data stored in the third buffer, the deviation of each of which exceeds a second upper limit or falls below a second lower limit, from the data stored in the third buffer, and storing the other of the data stored in the third buffer, in a fourth buffer; determining whether N2/N1 is within an allowable value or not, wherein the N2 is a number of the data stored in the fourth buffer; and when it is determined that the N2/N1 is within the allowable value, calculating data of average stroke volume variation based on the data stored in the fourth buffer.

The data of stroke volume variation may be calculated by measuring variation of a pulse wave propagation time of a patient based on correlation between a stroke volume and the pulse wave propagation time.

The data of stroke volume variation may be calculated by using an expression of SVV=2·(esSVmax−esSVmin)/(esSVmax+esSVmin), where SVV is stroke volume variation, esSVmax is maximum estimated stroke volume per respiratory rate, and esSVmin is minimum estimated stroke volume per respiratory rate.

The data of stroke volume variation may be data of arterial pulsation pressure variation which are calculated by measuring a pulse pressure of a blood pressure of a patient based on correlation between a stroke volume and the blood pressure.

The data of arterial pulsation pressure variation may be calculated by using an expression of PPV=2·(PPmax−PPmin)/(PPmax+PPmin), where PPV is arterial pulsation pressure variation, PPmax is maximum arterial pulsation pressure per mechanical respiratory rate, and PPmin is minimum arterial pulsation pressure per mechanical respiratory rate.

The data of stroke volume variation may be data of pulse wave amplitude variation which are calculated by measuring a pulse wave amplitude of a patient based on correlation between a stroke volume and the pulse wave amplitude.

The data of pulse wave amplitude variation may be calculated by an expression of PAV=100·(Pmax−Pmin)/meanP, where PAV is pulse wave amplitude variation, Pmax is maximum pulse wave amplitude per respiratory rate, Pmin is minimum pulse wave amplitude per respiratory rate, and meanP is average pulse wave amplitude per respiratory rate.

According to the invention, there is also provided a computer-readable recording medium in which a computer program causing a computer to execute the method is recorded.

According to the invention, there is also provided an blood volume measuring apparatus comprising: a buffer in which data of stroke volume variation at each respiratory rate are stored; and a controller: excludes data each of which has an abnormal value from a predetermined number of the data of stroke volume variation; excludes data each of which has an abnormal deviation from the data of stroke volume variation from which the data each of which has the abnormal value have been excluded; acquires a ratio of a number of the data of stroke volume variation data from which the data each of which has the abnormal deviation have been excluded, to the predetermined number; and performs calculation of data of an average stroke volume variation based on the data of stroke volume variation data from which the data each of which has the abnormal deviation have been excluded, when the ratio is within an allowable value.

DETAILED DESCRIPTION OF EMBODIMENTS

Figure 1:
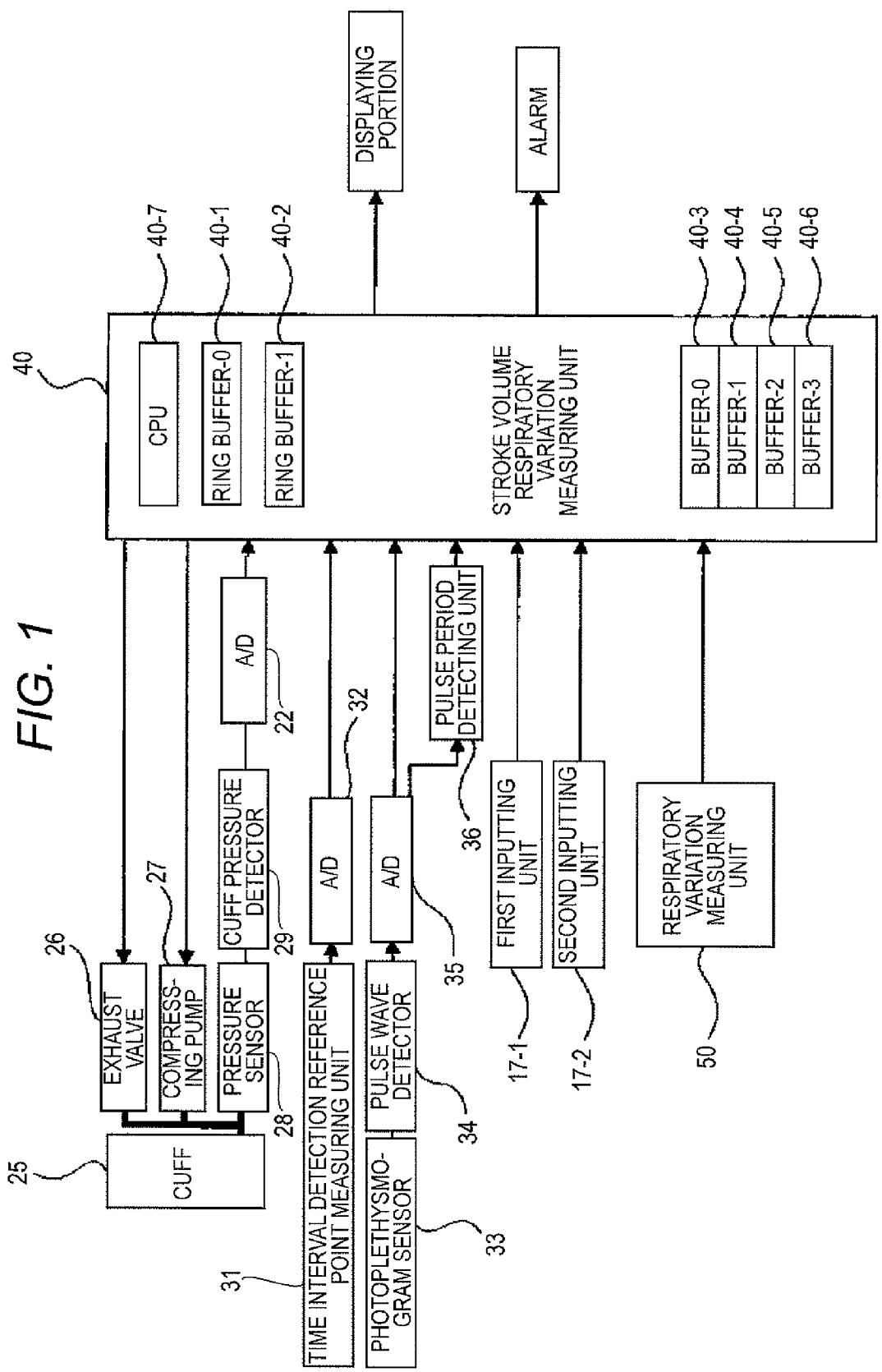
FIG. 1 is a block diagram illustrating the configuration of a biological signal monitoring apparatus according to the invention.

Next, an embodiment of a biological signal monitoring apparatus to which the present invention is applied will be described in detail with reference to the drawings. FIG. 1 is a block diagram illustrating the configuration of the biological signal monitoring apparatus according to the invention.

The biological signal monitoring apparatus includes a cuff 25, a compressing pump 27, a pressure sensor 28, a cuff pressure detector 29 and an A/D converter 22.

The cuff 25 is attached to an upper arm of the patient for measurement. In the cuff 25, the interior is opened or closed with respect to the atmosphere by an exhaust valve 26 installed in a body of the biological signal monitoring apparatus. Air is supplied to the cuff 25 by the compressing pump 27 installed in the body. The pressure sensor 28 is mounted in the body, and an output of the pressure sensor 28 is detected by the cuff pressure detector 29. An output of the cuff pressure detector 29 is converted into a digital signal by the A/D converter 22, and input to a stroke volume respiratory variation measuring unit 40.

The biological signal monitoring apparatus includes a time interval detection reference point measuring unit 31, an A/D converter 32, a photoplethysmogram sensor 33, a pulse wave detector 34, and an A/D converter 35.

The time interval detection reference point measuring unit 31 is used for detecting a point of time when an R wave is generated on an electrocardiogram, and the output thereof is converted into a digital signal by the A/D converter 32, and then input to the stroke volume respiratory variation measuring unit 40. The time interval detection reference point measuring unit 31 is configured by ECG electrodes which are attached to the chest of the patient. Measurement data is transmitted from a measurement data transmitter which is electrically connected to the ECG electrodes, to the body in a wireless manner. The transmitted measurement data is converted into a digital signal by the A/D converter 32 in the body, and then input to the stroke volume respiratory variation measuring unit 40. In this way, the ECG waveform is acquired.

Meanwhile, the photoplethysmogram sensor 33 is intended to be attached to a peripheral part, such as a finger, of the patient, and to be used in acquiring the pulse wave propagation time, for example, by performing SpO2 measurement. The measurement data of the photoplethysmogram sensor 33 is transmitted to the pulse wave detector 34 in the body in a wireless manner, whereby the pulse wave (photoplethysmogram) at the attachment location of the patient is detected. The output of the pulse wave detector 34 is converted into a digital signal by the A/D converter 35 and then input to the stroke volume respiratory variation measuring unit 40. As such, a waveform of the photoplethysmogram (a waveform at the periphery) is acquired.

The reference numeral 17-1 denotes a first inputting unit which is means for inputting the body surface area, age, and sexuality constituting the individual specific information that relates to oxygen metabolism of the patient. The reference numeral 17-2 denotes a second inputting unit which is means for inputting a timing of calibration.

The stroke volume respiratory variation measuring unit 40 includes a buffer in which the region is divided into a ring buffer-0 40-1, a ring buffer-1 40-2, a buffer-0 40-3, a buffer-1 40-4, a buffer-2 40-5, and a buffer-3 40-6, and a calculating unit (CPU) 40-7. The reference numeral 50 denotes a respiratory variation measuring unit.

Next, a method of removing an artifact in an analysis of respiratory variation of the stroke volume of the patient in order to determine the fluid response of the patient or adequately set artificial ventilation will be described.

A process in which data of stroke volume (esSV) synchronized with the pulse of the patient are acquired, and sequentially stored in the ring buffer-0 40-1 will be described with reference to the flowchart of FIG. 2.

A pulse synchronization detecting unit 36 in FIG. 1 determines whether pulse synchronization is detected or not (step S1).

Figure 11:
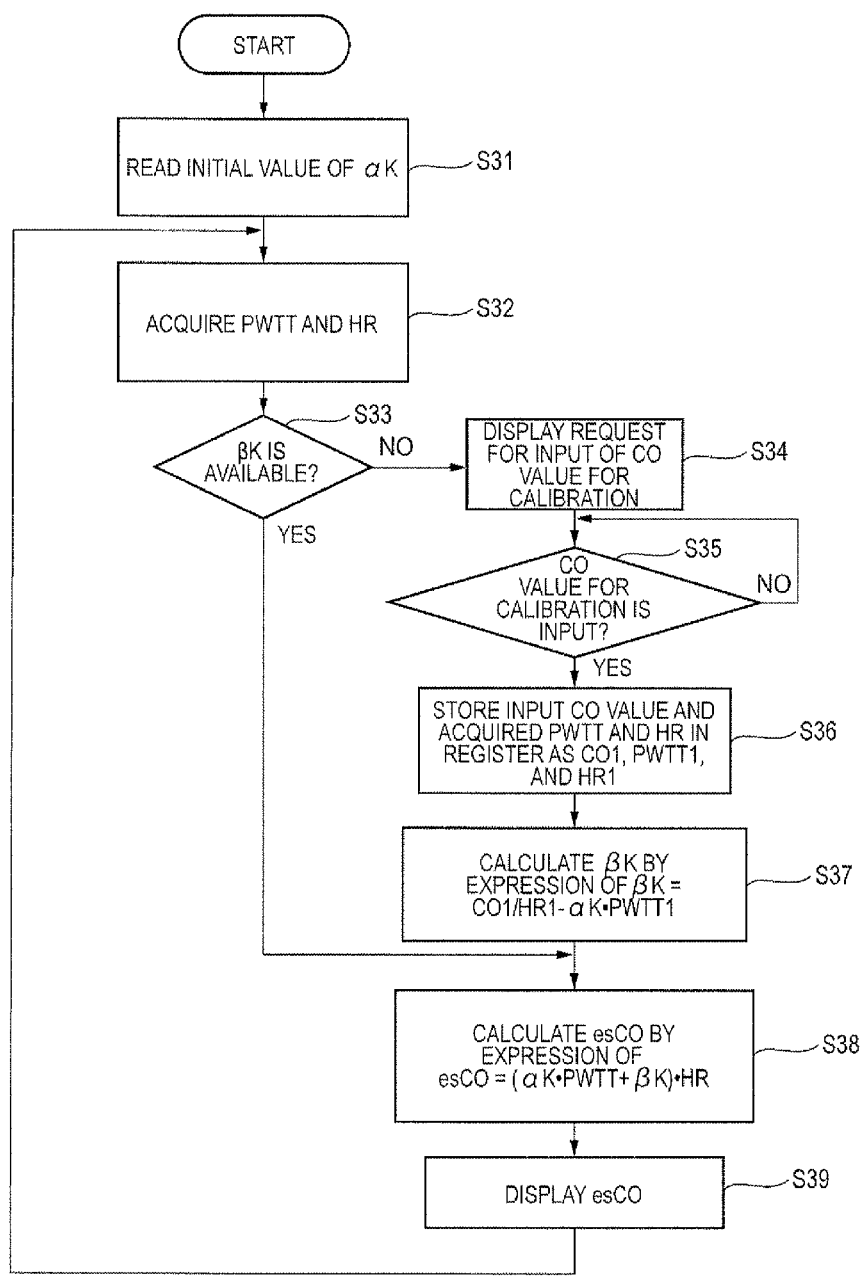
FIG. 11 is a flowchart showing a calculation process of acquiring esCO from $esCO=(\alpha K \cdot PWTT+\beta K) \cdot HR$ in the related-art biological signal monitoring apparatus of FIG. 8.

If the determination in Step S1 is Yes, data of esSV (corresponding to esCO in FIG. 11) is calculated, and stored in the ring buffer-0 40-1 (step S2).

The steps S1 and S2 are repeated, and the data of esSV at respective detections of pulse synchronization in the patient, are continuously stored in the ring buffer-0 40-1. The recording medium is configured by the ring buffers, and, when the number of the data of esSV exceeds a predetermined number, therefore, old data is overwritten with new data.

A process in which data of stroke volume variation (SVV) in one respiratory rate of the patient are acquired, and sequentially stored in the ring buffer-1 40-2 will be described with reference to the flowchart of FIG. 3.

The respiratory variation measuring unit 50 in FIG. 1 determines whether the end-tidal is detected or not (step S11).

If the determination in Step S11 is Yes, the data of esSV ranging from the timing of the immediately preceding end-tidal to that of the current end-tidal and stored in the ring buffer-0 40-1 are read, and then stored in the buffer-0 40-3 (step S12).

Based on the data of esSV for one respiratory stored in the buffer-0 40-3, data of SVV is calculated by an expression of SVV=2·(esSVmax−esSVmin)/(esSVmax+esSVmin) (step S13).

The data of SVV which is calculated in step S13 is stored in the ring buffer-1 40-2 (step S14).

The steps S11 to S14 are repeated, and the data of SVV at each respiratory of the patient are continuously stored in the ring buffer-1 40-2. The recording medium is configured by the ring buffers, and, when the number of the data of SVV exceeds a predetermined number, therefore, old data is overwritten with new data).

Next, the process of removing an artifact in an analysis of respiratory variation of the stroke volume of the patient will be described with reference to the flowchart of FIG. 4.

The respiratory variation measuring unit 50 in FIG. 1 determines whether the end-tidal is detected or not (step S21).

If the determination in Step S21 is Yes, it is determined whether the number of the data of SVV stored in the ring buffer-1 40-2 is equal to or larger than a number of N1 (for example, N1=64) or not (step S22).

If the determination in Step S22 is Yes, an N1 number of the data of SVV ranging from the present time to the past time and stored in the ring buffer-1 40-2 are stored in the buffer-1 40-4.

Data of SVV in which data of SVV values of which exceed a preset upper limit or fall below a preset lower limit are excluded as abnormal values from the N1 number of the data of SVV stored in the buffer-1 40-4 are stored in the buffer-2 40-5 (step S24).

The median value of values of the data of SVV stored in the buffer-2 40-5 is acquired, and deviations of the values of the data of SVV from the median value are acquired. Data of SVV in which data of SVV the acquired deviations of which exceed a preset upper limit (deviation upper limit) or fall below a preset lower limit (deviation lower limit) are excluded as abnormal deviations are stored in the buffer-3 40-6 (step S25).

The number of the data of SVV stored in the buffer-3 40-6 is indicated as N2 (step S26).

It is determined whether N2/N1 is within a predetermined allowable range (allowable average rate) or not (step S27).

If the determination in Step S27 is Yes, the data of SVV stored in the buffer-3 40-6 are averaged to calculate data of average SVV (avgSVV) (step S28).

If the determination in Step S27 is No, the calculation of the data of average SVV (avgSVV) is not performed (Step S29).

Figure 2:
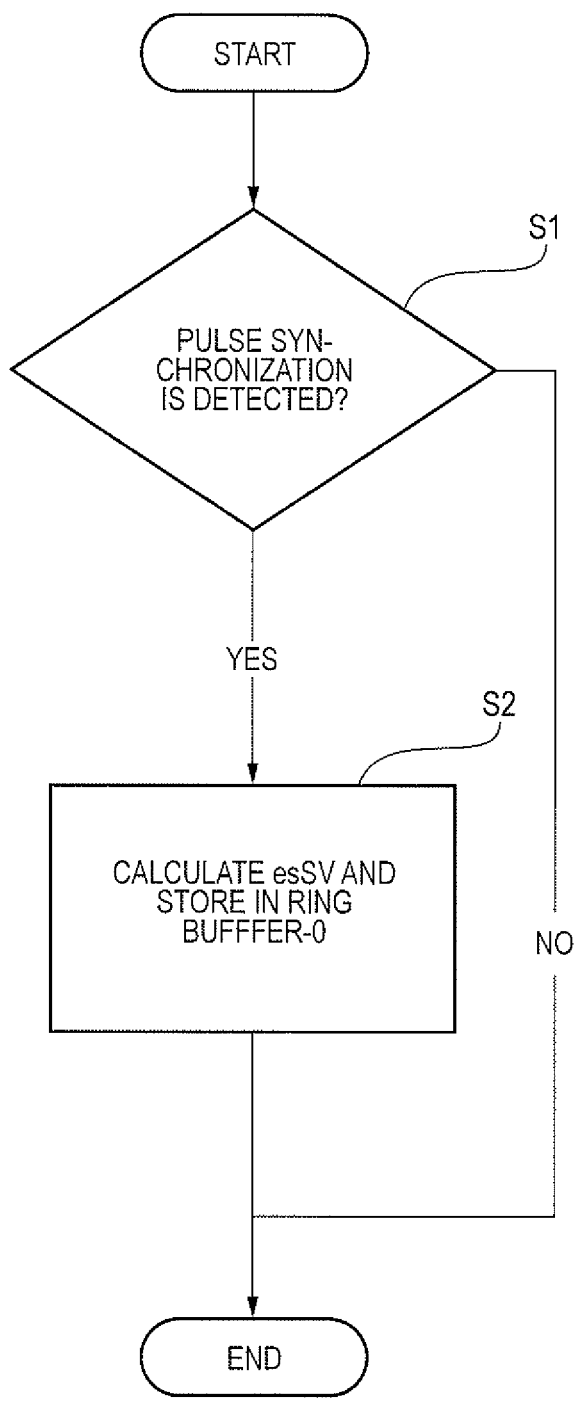
FIG. 2 is a flowchart showing a process in which data of stroke volume (esSV) synchronized with the pulse of the patient are acquired, and sequentially stored into a ring buffer.
Figure 3:
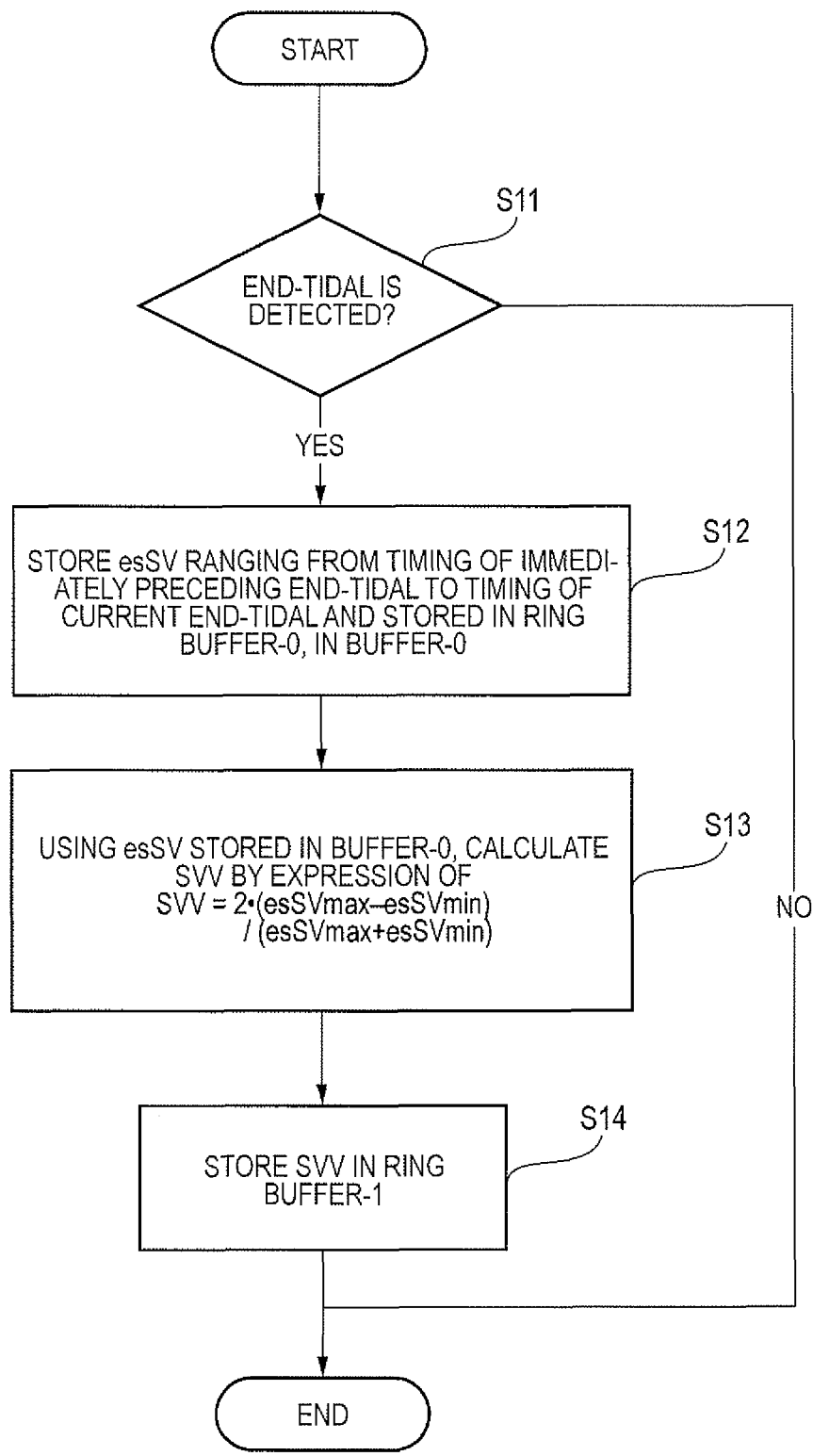
FIG. 3 is a flowchart showing a process in which data of stroke volume variation (SVV) in one respiratory rate of the patient are acquired, and sequentially stored in a ring buffer.
Figure 4:
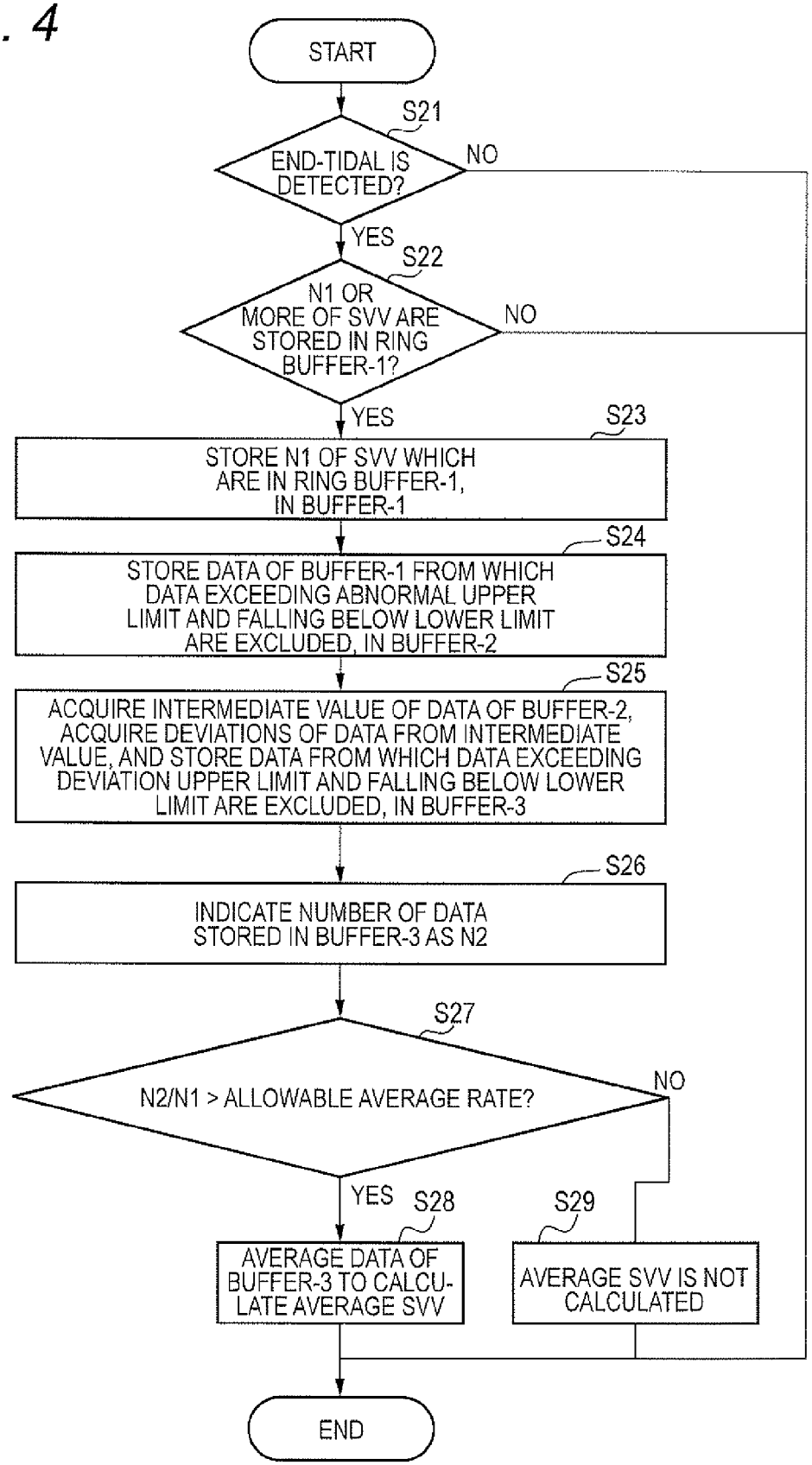
FIG. 4 is a flowchart illustrating a process of removing an artifact in an analysis of respiratory variation of the stroke volume which is acquired from the pulse wave propagation time by using correlation between the pulse wave propagation time and the stroke volume.

In the flowcharts of FIGS. 2 to 4, the process of removing an artifact in an analysis of respiratory variation of the stroke volume of the patient has been described by exemplifying the case where, by using correlation between the pulse wave propagation time and the stroke volume, respiratory variation of the stroke volume is measured from variation of the pulse wave propagation time. It is a matter of course that the invention is applicable also to the method where, by using correlation between the stroke volume and the blood pressure, the pulse pressure of the blood pressure of the patient is measured to measure respiratory variation of the stroke volume, and the PAD (Pulse Amplitude Deviation) method where, by using correlation between the amplitude of a peripheral pulse wave and the stroke volume, respiratory variation of the stroke volume is measured from variation of the pulse wave amplitude.

Figure 5A:
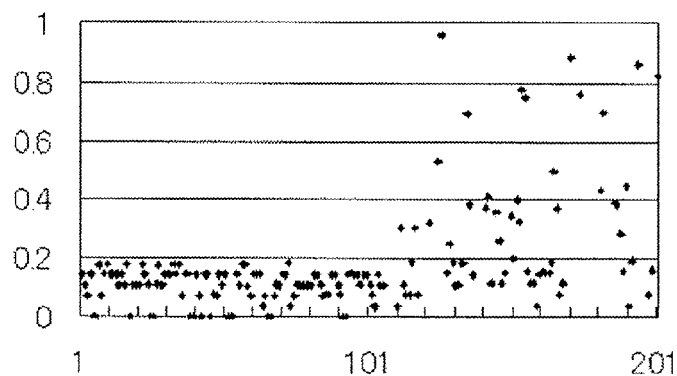
FIGS. 5A to 5C are views showing results of the process of removing an artifact in an analysis of respiratory variation of the stroke volume which is acquired from the pulse wave propagation time by using correlation between the pulse wave propagation time and the stroke volume.

Next, FIGS. 5A to 7C show results of the process of removing an artifact in the analysis of respiratory variation of the stroke volume of the patient in the flowcharts of FIGS. 2 to 4. FIGS. 5A to 5C show results of the process of removing an artifact in the analysis of respiratory variation of the stroke volume which is acquired from the variation of the pulse wave propagation time by using correlation between the pulse wave propagation time and the stroke volume.

Figure 5B:
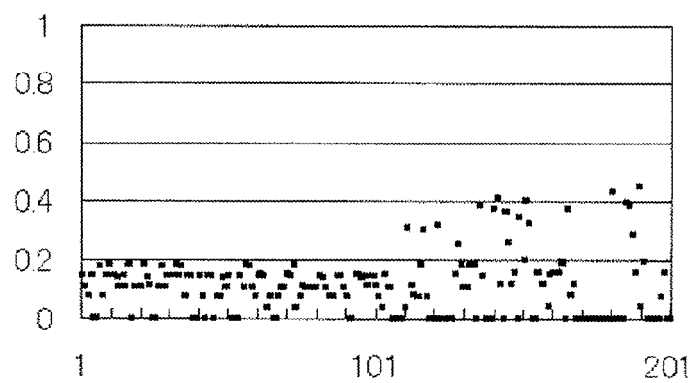
Figure 5C:
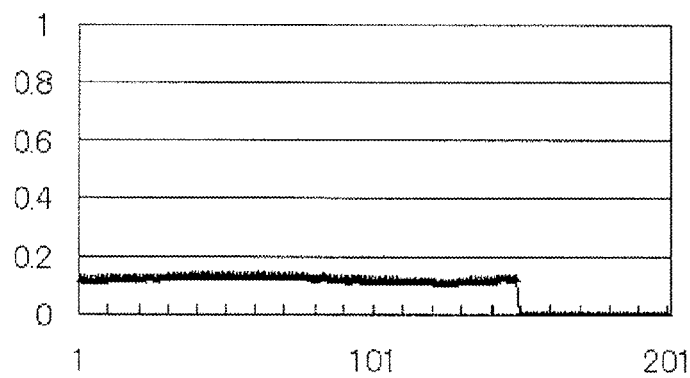

The set values in the graphs of FIGS. 5A to 5C are as follows:

N1 in step S22 is N1=64;

The abnormal upper and lower limits in step S24 are Upper limit=0.45 and Lower limit=0;

The deviation upper and lower limits in step S25 are Deviation upper limit=0.1 and Deviation lower limit=−0.1; and An allowable average rate in step S27 is Allowable average rate=0.75.

FIG. 5A shows a graph indicating data of SVV acquired in each respiratory rate. These individual data are stored in the ring buffer-1 40-2.

FIG. 5B shows a graph indicating data of SVV1 which are results of the process where the abnormal upper and lower limits in step S24 are set to Upper limit=0.45 and Lower limit=0. These individual data are stored in the buffer-2 40-5.

FIG. 5C shows a graph indicating data of avgSVV which are results of the process where the deviation upper and lower limits in steps S25 to S28 are Deviation upper limit=0.1, Deviation lower limit=−0.1, and Allowable average rate=0.75.

Figure 6A:
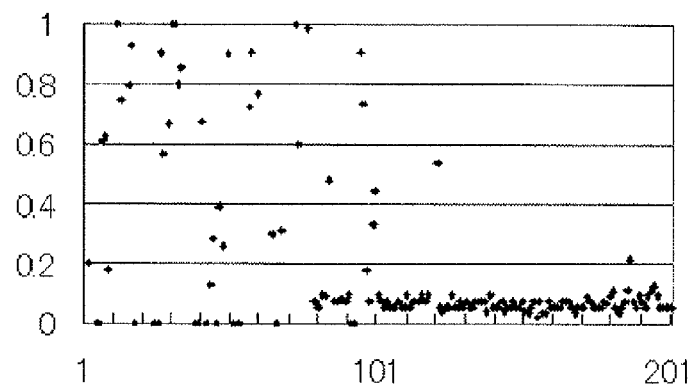
FIGS. 6A to 6C are views showing results of a process of removing an artifact in an analysis of respiratory variation of the stroke volume in a method of, by using correlation between the stroke volume and the blood pressure, measuring the pulse pressure of the blood pressure of the patient to measure respiratory variation of the stroke volume.
Figure 6B:
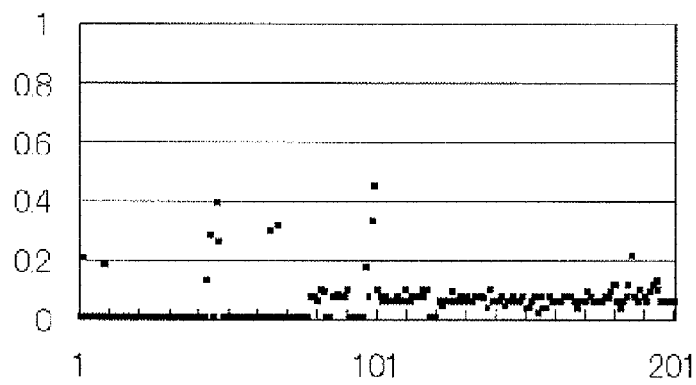
Figure 6C:
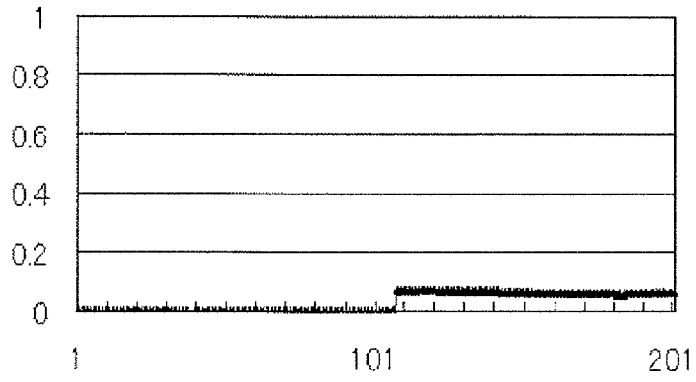

FIGS. 6A to 6C show results of the process of removing an artifact in an analysis of respiratory variation of the stroke volume in the method of, by using correlation between the stroke volume and the blood pressure, measuring the pulse pressure of the blood pressure of the patient to measure respiratory variation of the stroke volume.

The set values in the graphs of FIGS. 6A to 6C are as follows:

N1 in step S22 is N1=64;

The abnormal upper and lower limits in step S24 are Upper limit=0.45 and Lower limit=0;

The deviation upper and lower limits in step S25 are Deviation upper limit=0.1 and Deviation lower limit=−0.1; and An allowable average rate in step S27 is Allowable average rate=0.75.

FIG. 6A shows a graph indicating data of PPV acquired in each respiratory rate. These individual data are stored in the ring buffer-1 40-2.

FIG. 6B shows a graph indicating data of PPV1 which are results of the process where the abnormal upper and lower limits in step S24 are set to Upper limit=0.45 and Lower limit=0. These individual data are stored in the buffer-2 40-5.

FIG. 6C shows a graph indicating data of avgPPV which are results of the process where the deviation upper and lower limits in steps S25 to S28 are Deviation upper limit=0.1, Deviation lower limit=−0.1, and Allowable average rate=0.75.

Figure 7A:
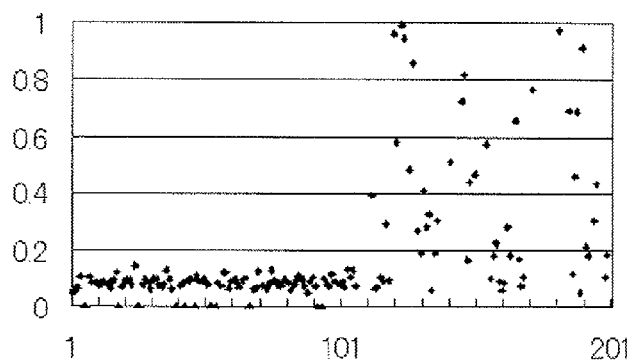
FIGS. 7A to 7C are views showing results of a process of removing an artifact in an analysis of respiratory variation of the stroke volume in the PAD (Pulse Amplitude Deviation) method in which, by using correlation between the amplitude of a peripheral pulse wave and the stroke volume, respiratory variation of the stroke volume is measured from variation of the pulse wave amplitude.
Figure 7B:
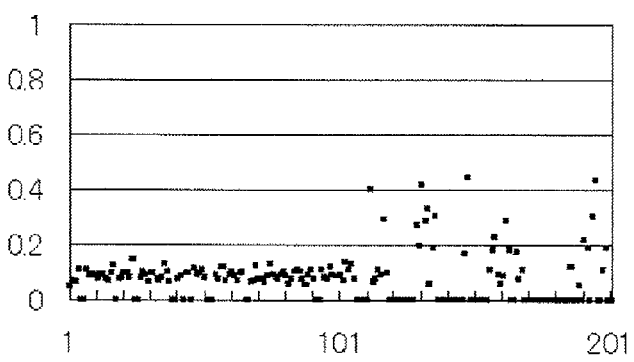
Figure 7C:
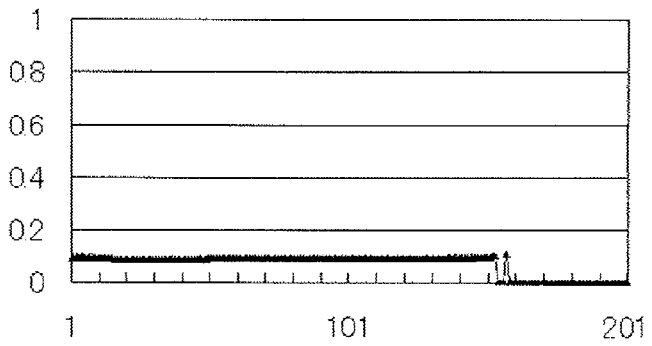
Figure 8:
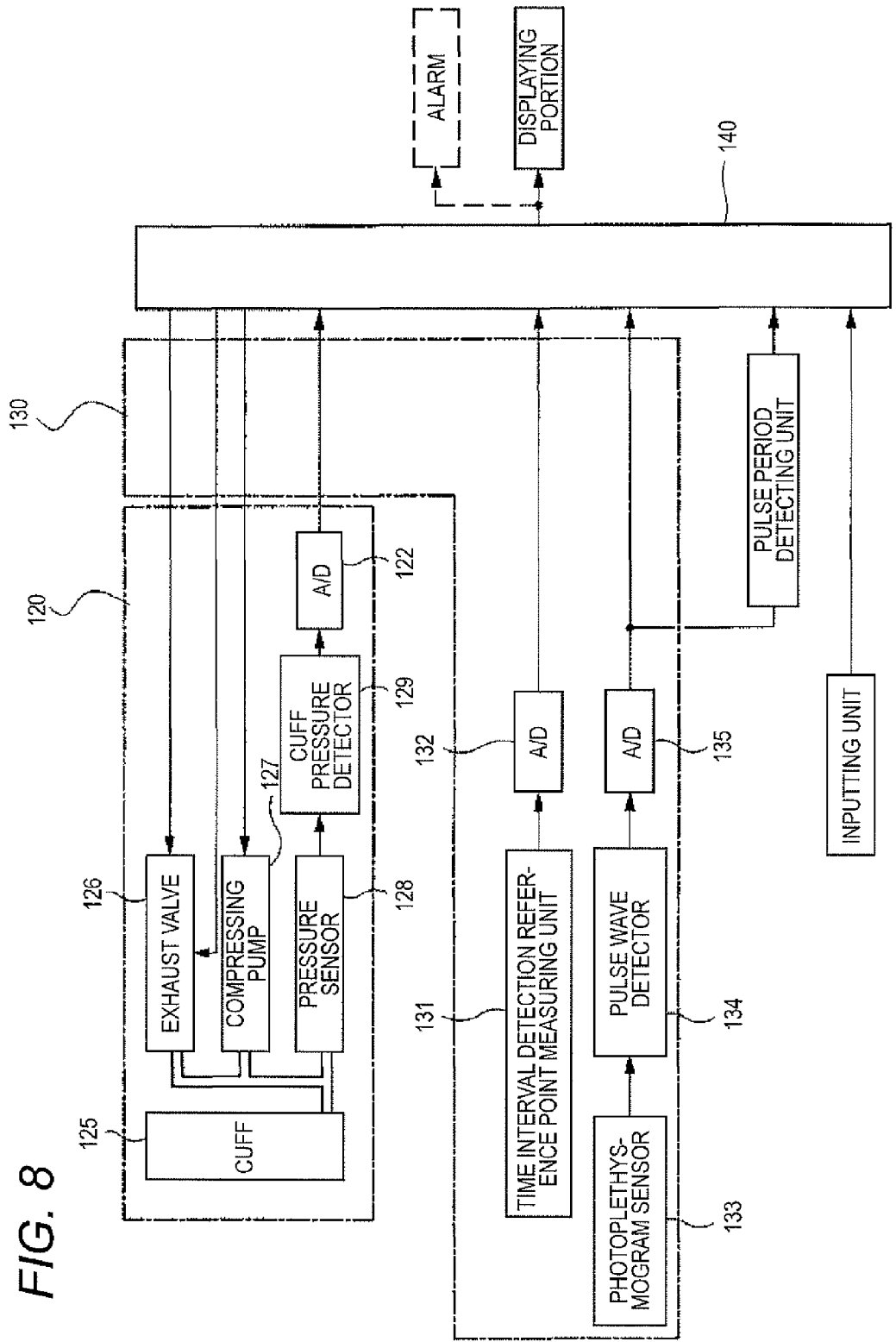
FIG. 8 is a block diagram illustrating the configuration of a related-art biological signal monitoring apparatus.
Figure 9:
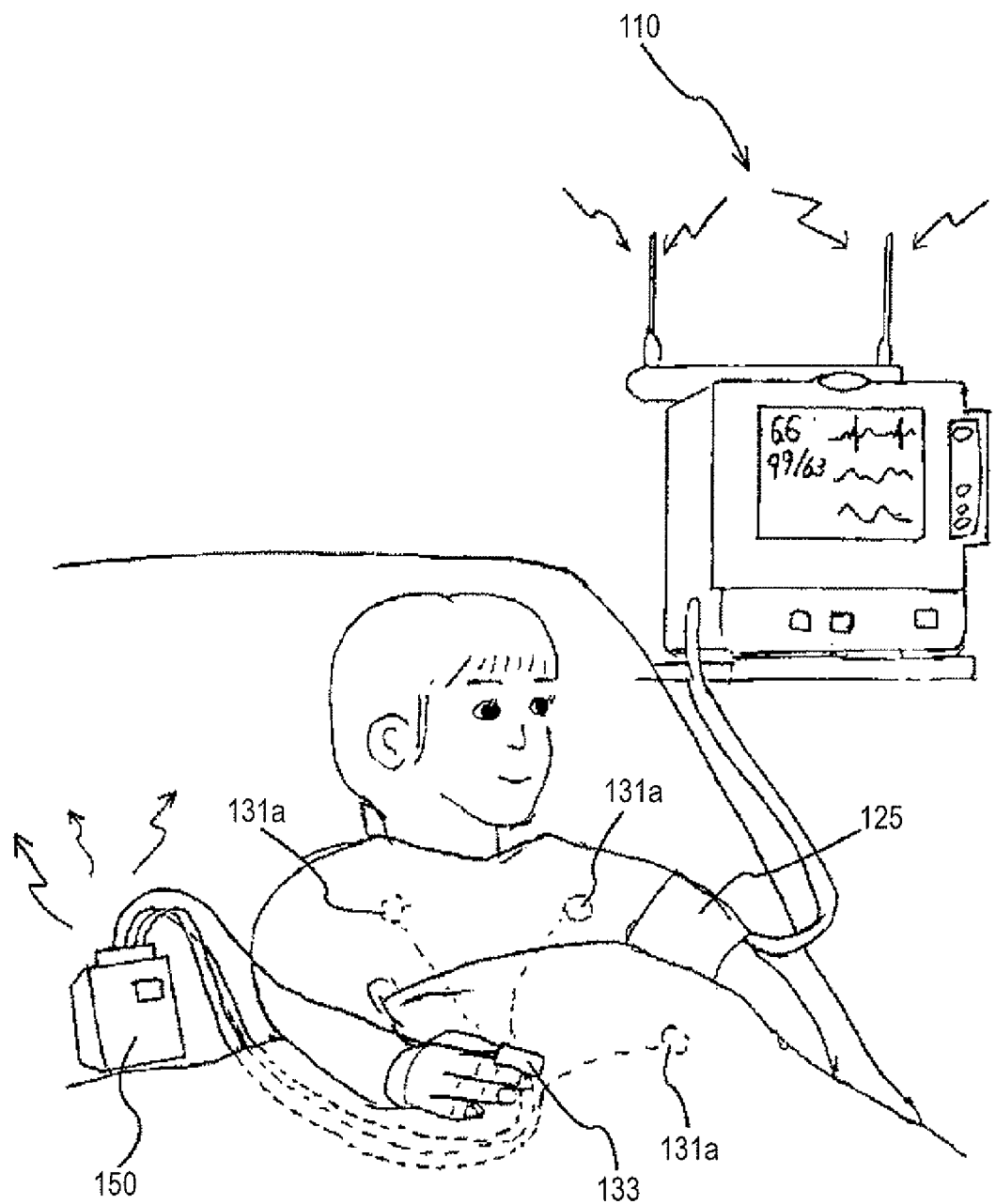
FIG. 9 is a view showing an example of a measurement mode in the related-art biological signal monitoring apparatus of FIG. 8.
Figure 10:
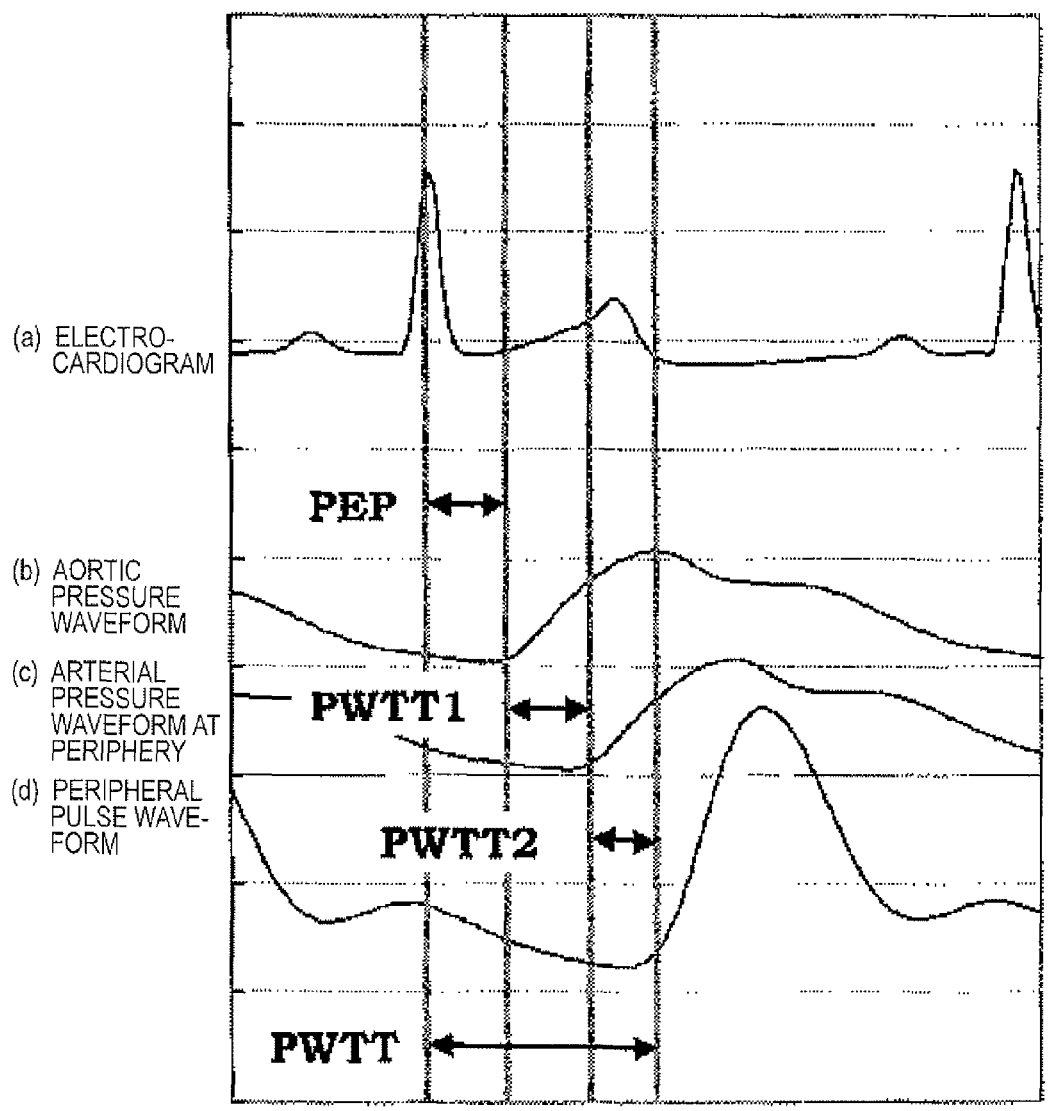
FIG. 10 is a view showing waveforms of pulse waves measured in the related-art biological signal monitoring apparatus of FIG. 8.

FIGS. 7A to 7C show results of the process of removing an artifact in an analysis of respiratory variation of the stroke volume in the PAD (Pulse Amplitude Deviation) method in which, by using correlation between the amplitude of a peripheral pulse wave and the stroke volume, respiratory variation of the stroke volume is measured from variation of the pulse wave amplitude.

The set values in the graphs of FIGS. 7A to 7C are as follows:

N1 in step S22 is N1=64;

The abnormal upper and lower limits in step S24 are Upper limit=0.45 and Lower limit=0;

The deviation upper and lower limits in step S25 are Deviation upper limit=0.1 and Deviation lower limit=−0.1; and An allowable average rate in step S27 is Allowable average rate=0.75.

FIG. 7A shows a graph indicating data of PAV acquired in each respiratory rate. These individual data are stored in the ring buffer-1 40-2.

FIG. 7B shows a graph indicating data of PAV1 which are results of the process where the abnormal upper and lower limits in step S24 are set to Upper limit=0.45 and Lower limit=0. These individual data are stored in the buffer-2 40-5.

FIG. 7C shows a graph indicating avgPAV data which are results of the process where the deviation upper and lower limits in steps S25 to S28 are Deviation upper limit=0.1, Deviation lower limit=−0.1, and Allowable average rate=0.75.

As shown in FIGS. 7A to 7C, it can be seen that, in the analysis of respiratory variation of the stroke volume according to the invention, an artifact is removed more satisfactorily.

According to an aspect of the invention, it is expected that the resolution will be improved to about $1/\sqrt{N2}$.

According to an aspect of the invention, it is possible to realize a method, apparatus and program of removing an artifact which, in an apparatus for analyzing respiratory variation of the stroke volume of the patient in order to determine the fluid response of the patient or adequately set artificial ventilation, can accurately remove an artifact without requiring an expensive A/D converter having a high resolution.

What is claimed is:

1. A blood volume measuring method, that includes removing an artifact in analysis of respiratory variation of a stroke volume of a patient, comprising:
   acquiring data of stroke volume variation at each respiratory rate, and storing the acquired data in a first buffer;
   reading an N1 number of the data stored in the first buffer, from the first buffer, and storing the N1 number of the data in a second buffer;
   excluding a part of the data stored in the second buffer, a value of each of which exceeds a first upper limit or falls below a first lower limit, from the data stored in the second buffer, and storing a remainder of the data stored in the second buffer, in a third buffer;
   acquiring a deviation of each of the data stored in the third buffer, from a median value of the data stored in the third buffer, excluding a part of the data stored in the third buffer, the deviation of each of which exceeds a second upper limit or falls below a second lower limit, from the data stored in the third buffer, and storing a remainder of the data stored in the third buffer, in a fourth buffer;
   removing the artifact of respiratory variation of a stroke volume by determining whether N2/N1 is within an allowable value or not,
   wherein the N2 is a number of the data stored in the fourth buffer; and
   when it is determined that the N2/N1 is within the allowable value, determining respiratory variation of the stroke volume by calculating data of average stroke volume variation based on the data stored in the fourth buffer to determine a fluid response of the patient or adequately set artificial ventilation; and
   when it is determined that a fluid response of the patient is positive based on the determined respiratory variation of the stroke volume, performing fluid administration, or when it is determined that setting of artificial ventilation is not adequate based on the determined respiratory variation of the stroke volume, changing the setting of the artificial ventilation.

2. The blood volume measuring method according to claim 1, wherein the data of stroke volume variation are calculated by measuring variation of a pulse wave propagation time of a patient based on correlation between a stroke volume and the pulse wave propagation time.

3. The blood volume measuring method according to claim 2, wherein the data of stroke volume variation are calculated by using an expression of $SVV = 2 \cdot (esSVmax - esSVmin)/(esSVmax + esSVmin)$, where SVV is stroke volume variation, esSVmax is maximum estimated stroke volume per respiratory rate, and esSVmin is minimum estimated stroke volume per respiratory rate.

4. The blood volume measuring method according to claim 1, wherein the data of stroke volume variation are data of arterial pulsation pressure variation which are calculated by measuring a pulse pressure of a blood pressure of a patient based on correlation between a stroke volume and the blood pressure.

5. The blood volume measuring method according to claim 4, wherein the data of arterial pulsation pressure variation are calculated by using an expression of $PPV = 2 \cdot (PPmax - PPmin)/(PPmax + PPmin)$, where PPV is arterial pulsation pressure variation, PPmax is maximum arterial pulsation pressure per mechanical respiratory rate, and PPmin is minimum arterial pulsation pressure per mechanical respiratory rate.

6. The blood volume measuring method according to claim 1, wherein the data of stroke volume variation are data of pulse wave amplitude variation which are calculated by measuring a pulse wave amplitude of a patient based on correlation between a stroke volume and the pulse wave amplitude.

7. The blood volume measuring method according to claim 6, wherein the data of pulse wave amplitude variation are calculated by an expression of $PAV = 100 \cdot (Pmax - Pmin)/meanP$, where PAV is pulse wave amplitude variation, Pmax is maximum pulse wave amplitude per respiratory rate, Pmin is minimum pulse wave amplitude per respiratory rate, and meanP is average pulse wave amplitude per respiratory rate.

8. A non-transitory computer-readable recording medium in which a computer program causing a computer to execute the method according to claim 1 is recorded.

9. A blood volume measuring apparatus, that includes removing an artifact in analysis of respiratory variation of a stroke volume of a patient, comprising:
- a buffer in which data of stroke volume variation at each respiratory rate are stored; and
- a controller that:
  - excludes data each of which has an abnormal value from a predetermined number of the data of stroke volume variation;
  - excludes data each of which has an abnormal deviation from the data of stroke volume variation from which the data each of which has the abnormal value have been excluded;
  - acquires a ratio of a number of the data of stroke volume variation data from which the data each of which has the abnormal deviation have been excluded, to the predetermined number;
  - determines respiratory variation of the stroke volume by performing calculation of data of an average stroke volume variation based on the data of stroke volume variation data from which the data each of which has the abnormal deviation have been excluded, when the ratio is within an allowable value; and
- when it is determined that a fluid response of the patient is positive based on the determined respiratory variation of the stroke volume, performs fluid administration, or when it is determined that setting of artificial ventilation is not adequate based on the determined respiratory variation of the stroke volume, changes the setting of the artificial ventilation.

* * * * *